United States Patent [19]

Shields

[11] Patent Number: 4,663,530
[45] Date of Patent: May 5, 1987

[54] QUANTITATIVE MEASUREMENT OF FAT IN DAIRY PRODUCTS

[76] Inventor: John Shields, c/o Shields Instruments Limited, Wheldrake, York Y04 6NA, England

[21] Appl. No.: 842,312

[22] Filed: Mar. 21, 1986

Related U.S. Application Data

[63] Continuation-in-part of Ser. No. 596,893, Apr. 5, 1984, abandoned.

[30] Foreign Application Priority Data

May 4, 1983 [GB] United Kingdom ................. 8309153

[51] Int. Cl.⁴ .............................................. G01J 1/00
[52] U.S. Cl. .................................... 250/339; 250/343
[58] Field of Search ............................... 250/339, 343

[56] References Cited

U.S. PATENT DOCUMENTS

| | | | |
|---|---|---|---|
| 4,076,983 | 2/1978 | Hopkins et al. | 250/343 |
| 4,207,469 | 6/1980 | Hopkins et al. | 250/343 |
| 4,247,773 | 1/1981 | Neko et al. | 250/339 |
| 4,310,763 | 1/1982 | Shields | 250/339 |
| 4,447,725 | 5/1984 | Biggs et al. | 250/343 |

OTHER PUBLICATIONS

Smith et al., "Fatty Acid Composition of the Phospholipids and Other Lipids in Milk," 1/22/62, pp. 581–588.
Goulden, "Infrared Spectroscopy of Dairy Products", 9/7/56, pp. 609–613.
Conley, "Infrared Spectroscopy", 1/4/74, Second Edition, pp. 92–93.

Primary Examiner—Janice A. Howell
Attorney, Agent, or Firm—Barnes, Kisselle, Raisch, Choate, Whittemore & Hulbert

[57] ABSTRACT

An infrared transmission/absorption technique for the quantitative determination of fat in dairy products, particularly high-fat dairy products having fat concentrations between 15 and 60 w/o. A wave band characteristic of bending and scissoring of saturated carbon hydrogen bonds is employed, preferably a wave band at about 6.84 microns. It is further preferred to use the double wavelength, single cuvette system. Variations in accuracy caused by lipolysis and degree of homogenization are substantially reduced.

14 Claims, 6 Drawing Figures

QUANTITATIVE MEASUREMENT OF FAT IN DAIRY PRODUCTS

This application is a continuation-in-part of application Ser. No. 596,893 filed Apr. 5, 1984, now abandoned.

The present invention relates to spectrophotometric measurement of fat concentration in dairy products, particularly high-fat dairy products such as cream and ice cream.

BACKGROUND OF THE INVENTION

Pioneer efforts in spectrophotometric analysis of dairy products are reported in Goulden, "Infra-red Spectroscopy of Dairy Products," *J. Sci. Food Agric.*, Sept. 7, 1956, pp. 609-613. In this paper, Dr. Goulden reported milkfat absorption peaks or "shoulders" at wave numbers of about 2900 to 2850 cm$^{-1}$, 1740 cm$^{-1}$ and 1465 cm$^{-1}$, among others, corresponding to wavelengths of 3.48 microns, 5.73 microns and 6.83 microns respectively. Absorption at the 6.83 micron wavelength was shown to be relatively weak as compared with those at the 3.48 and 5.73 micron bands. Dr. Goulden also reported in U.S. Pat. No. 3,161,768 that, due to the so-called Christenson light-scattering effect of milkfat globules, it is necessary that the fat measurement wavelength be at least three times the average globule diameter to obtain accurate fat assessments employing this technique. Given the state of the homogenization art at that time, and in view of absorption characteristics of water, the major component of milk, the wavelength of 5.73 microns, characteristic of ester linkages in the triglyceride portion of the fat molecule, was selected as "most convenient."

Thus, Goulden U.S. Pat. No. 3,161,768 and "The Infra Red Milk Analyzer," *J. Soc. Dairy Tech,* 17, 1 (1964) p. 28–33 disclose an analyzer for measuring concentrations of fat, protein, lactose and non-fat solids in dairy products. This analyzer, marketed under the trademark IRMA, measured absorption of infrared energy at selected wavelengths characteristic of each constituent, and cross-corrected among the raw fat, protein and lactose readings for effects due to the other constituents. Subsequent advances in the art of small homogenizers suitable for use in devices of this type yielded milkfat particle sizes of 1.2 microns or less. Such a homogenizer was contained, for example, in the Milko-Scan unit described as prior art in Nexo et al U.S. Pat. No. 4,247,773. According to the teaching of Dr. Goulden that particle size must be no more than about ⅓ of the milkfat measurement wavelength, it was then feasible to measure milkfat accurately at the 3.48 micron wave band disclosed by Dr. Goulden characteristic of stretching of carbon-hydrogen bonds in the fatty acid chain. Thus, the Nexo et al patent discloses a milkfat measurement technique wherein measurements are performed at the 3.48 micron wavelength rather than the 5.73 micron wavelength of the IRMA and prior Milko-Scan units.

Each of the 3.48 and 5.73 micron wavelengths possesses advantages and disadvantages relative to measurement of milkfat concentration. The 5.73 micron wavelength is responsive to triglycerides, specifically ester linkages, in the milkfat molecules, but substantially independent of variations in fatty acid chain length. Stated differently, 5.73 micron wavelength measurement assumes uniform mean molecular weight. However, genetic variations among cow breeds and the practice of employing differing feedstuffs have caused significant variation in mean molecular weight of milkfat among differing herds. The 3.48 micron wavelength, on the other hand, is responsive to stretching of saturated carbon-hydrogen bonds in the milkfat molecule, and thus is more closely, but not precisely, responsive to variations in fatty acid chain length. However, measurement at the 3.48 micron wavelength is subject to substantial variation due to natural variations in degree of saturation and the number of hydroxyl and methyl groups per molecule. In addition, 3.48 micron wavelength measurements vary significantly with protein and lactose concentrations, rendering cross-correction more difficult. Thus, the 3.48 micron wavelength technique is of little value as applied to skim milk products, where lactose, protein and water concentrations greatly overshadow fat concentration, and in synthetic dairy products prepared with polyunsaturated vegetable oils.

A detailed scientific study of the causes of inaccuracy of the 3.48 and 5.73 micron measurement techniques by Prof. D. Biggs led to the discovery that, while both measurements are sensitive to changes in molecular weight, the variations are of opposite sign. This observation of scientific fact led to the realization that both the 3.48 and 5.73 micron measurements are based upon absorbances which represent only a portion of the whole milkfat molecule, and that the magnitude of the errors of each are proportional to the variation in weight of these portions or weight fractions of the molecule as a function of total weight of the molecule. Thus, Biggs et al U.S. Pat. No. 4,447,725 discloses a technique for measuring milkfat as a conjoint function of the 3.48 and 5.73 measurement readings. This technique is substantially independent of molecular weight variations and, as implemented in the apparatus disclosed in Shields U.S. Pat. No. 4,310,763 and 4,418,809 and marketed by applicant under the trademark MULTISPEC, has enjoyed substantial commercial acceptance and success in the dairy industry where compensation to milk producers is based in substantial part by law on fat concentration.

However, other problems inherent in the 3.48 and 5.73 micron measurement techniques have remained unresolved. For example, lipolysis of the triglycerides, which increases with age and poor storage, among other factors, causes deesterification of the ester linkages in the carbonyl ester bonds, and thus decreases accuracy of the 5.73 micron measurement. Accuracy of the 3.48 micron reading likewise declines, and the two inaccuracies are not of opposite sign as with molecular weight variations. Thus, even the conjoint measurement technique of Biggs et al does not accommodate inaccuracies due to lipolysis. Another problem lies in control of homogenization. Although reduction of milkfat particles to less than 1.2 microns is well within conventional technology, maintenance of this level presents difficulties as the homogenizer ages and/or is not properly maintained or operated. It is desirable to decrease such dependence of measurement accuracy upon homogenization. Another problem, which applies particularly to high-volume automated testing laboratories, lies in the fact that the Biggs et al technique requires two fat measurements, increasing the sample through-put time by ⅓ for measurement of fat, protein and lactose.

Concentration of fat in milk produced by typical cow breeds averages about 3.7 weight percent (w/o). In some cow breeds, concentration can range up to 8 to 9 w/o. For Indian buffalo, milkfat concentrations up to 12 w/o are typical. The extinction or absorption coefficients at the 3.48 and 5.73 micron wavelengths are such that measurements may be performed accurately and with high resolution on dairy products having milkfat concentration up to 15 w/o employing the standard MULTIPSEC thirty-seven micron-thick sample cell. However, such measurements cannot be readily performed on high-fat dairy products, such as ice cream and cream, because the extinction coefficients at the 3.48 and 5.73 micron wavelength are such that energy is substantially completely absorbed at 15 w/o, and therefore yields little resolution above this concentration. Use of a thinner sample would reduce absolute absorption and increase measurement range, but would also lead to clogging of the cell. Thus, it has become standard practice for persons wishing to measure milkfat concentrations in products above 15 w/o fat to dilute the product at predetermined ratio to obtain samples for test. Such dilution is time consuming and subject to inaccuracy.

OBJECTS AND SUMMARY OF THE INVENTION

It is therefore a general object of the present invention to provide a technique for quantitative assessment of milkfat by infrared transmission/absorption which reduces or overcomes the aforementioned problems of lipolysis, homogenization and/or production throughput which inhere in the prior art.

It is a more specific object of the present invention to provide a technique for direct infrared spectrophotometric analysis of milkfat in dairy products such as cream and ice cream having milkfat concentrations in excess of 15 w/o, specifically between 15 and 60 w/o, in standard test apparatus and without requiring dilution or other fat-reducing preparations.

In accordance with the present invention, concentration of milkfat in dairy products is quantitatively measured or assessed, employing otherwise conventional techniques, but at a measurement wavelength characteristic of bending and scissoring of saturated carbon-hydrogen bonds in the fatty acid chain. This measurement is preferably performed in the range of 6.75 to 7.1 microns, and most preferably at about 6.84 microns. Reference wavelength for the milkfat measurement is preferably in the range of 6.46 to 6.75 microns or 7.0 to 7.20 microns, and most preferably in the range of about 7.11 to 7.15 microns.

One particularly important aspect of the invention contemplates a method for measuring milkfat concentrations in excess of 15 w/o in dairy products. Infrared energy in a wave band characteristic of bending and scissoring of carbon-hydrogen bonds (preferably 6.84 microns) is transmitted through a test sample, and milkfat concentration is quantitatively assessed as a function of energy absorbed. As noted above, Dr. Goulden discloses an absorption peak at about this wavelength, but possessing a weak extinction coefficient. However, in accordance with this aspect of the present invention, this seeming disadvantage is employed to advantage in that enhanced resolution and accuracy are obtained in high-fat products. Stated differently, whereas the 3.48 and 5.73 micron wavelengths are almost completely absorbed at 15 w/o milkfat and yield negligible resolution beyond this point, the weak extinction coefficient at the 6.84 micron wavelength yields low absorption and less than ideal results up to 15 w/o, but excellent results and high accuracy and resolution above 15 w/o, particularly between 15 and 60 w/o. Thus, the invention may be readily implemented using standard equipment and sample cells without requiring dilution of the test materials.

A further advantage of measuring milkfat at the 6.84 micron wavelength is that absorbance due to water is relatively less than at the 3.48 micron wavelength with the result that the effect of water-displacing components such as mineral salts and other milk components is relatively less, and more initial energy is transmitted through the sample so that a greater signal is available for fat measurement. Moreover, measurement at the preferred 6.84 micron wavelength is less affected by lipolysis than at either of the 3.48 or 5.73 micron wavelengths. Furthermore, measurement at the 6.84 micron wavelength is less dependent upon homogenization than with either of the 3.48 and 5.73 micron wavelengths. Indeed, little or no homogenization is required.

Most preferably, the invention is implemented employing so-called double-beam/single-cell principles as disclosed in the above-noted Shields and Biggs et al patents. Infrared energy is sequentially transmitted through a test cell at a measurement wavelength for each constituent of interest (fat, protein and lactose) and at an adjacent reference wavelength at which absorbance is less dependent upon the measured constituent. A raw constituent reading is then obtained as a function of comparative absorption therebetween. Correction is performed employing standard cross-correlation techniques.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF PREFERRED EMBODIMENTS

The above-referenced patents to Shields and Biggs et al are incorporated herein by reference. Measurements in the following examples were performed on an instrument marketed under the trademark MULTISPEC by applicant in accordance with the teachings of the referenced patents.

EXAMPLE 1

Figure 1:
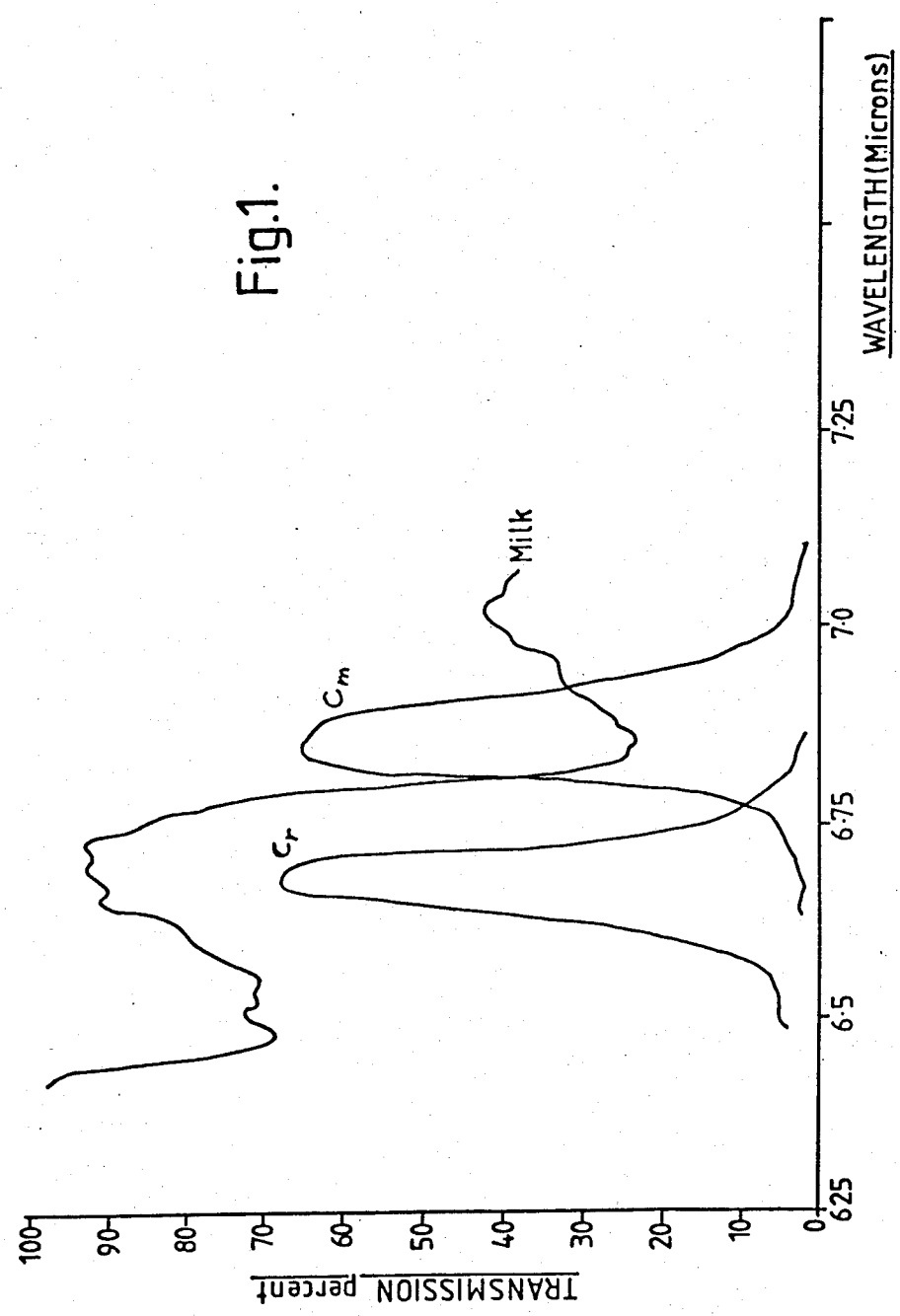
FIG. 1 shows an infrared absorption difference spectrum of milk against water.

A standard MULTISPEC milk analyzer instrument was fitted with two filters having transmission characteristics Cm and Cr (FIG. 1), the sample measurement filter having transmission characteristics Cm in the wave band about 6.84 microns, and the reference filter having transmission Cr in the band about 6.67 microns. FIG. 1 also shows the absorption difference spectrum of a milk sample with respect to water in the range 6.25 to 7.25 microns. It can be seen that the absorption of the milk sample at the wavelength of filter Cm is very much greater than that of filter Cr, enabling comparative measurements to be obtained.

The instrument was first linearized in the normal manner. A correlation coefficient of 0.99997 over the range 0% to 10% milkfat was achieved when comparing uncorrected instrument results against a linear dilution series of samples. The instrument was then calibrated in the normal way using the multiple regression program built into existing software. The regression program determines a slope value for the signal obtained from the filter pair and derives interference coefficients due to the other components in the mixture which, when introduced into Equation (1), enable the instrument to quantify fat.

$$F_c = aF_o + bP_o + cL_o \quad (1)$$

where $F_o$, $P_o$ and $L_o$ are raw instrument readings for fat, protein and lactose respectively, and "a," "b" and "c" are correction coefficients. The results of the above calibration are shown in Table 1.

Figure 4:
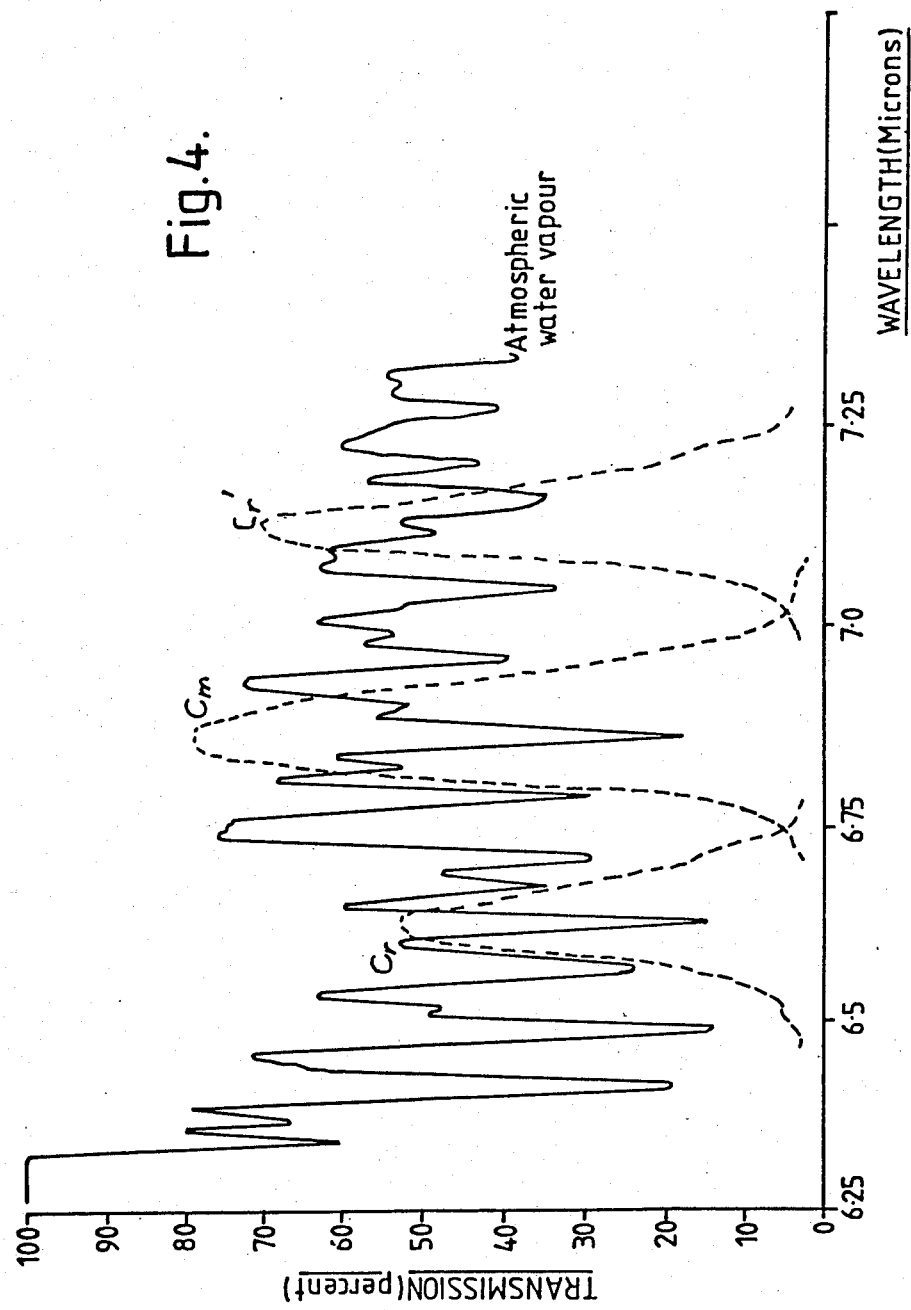
FIG. 4 illustrates a spectrum for atmospheric water vapor.

Referring to FIG. 4, it will be observed that there is a good balance between water vapor absorbance at filter Cm and filter Cr transmission envelopes. This was verified in practice as drying and wetting of the instrument caused negligible change in response.

EXAMPLE 2

Figure 2:
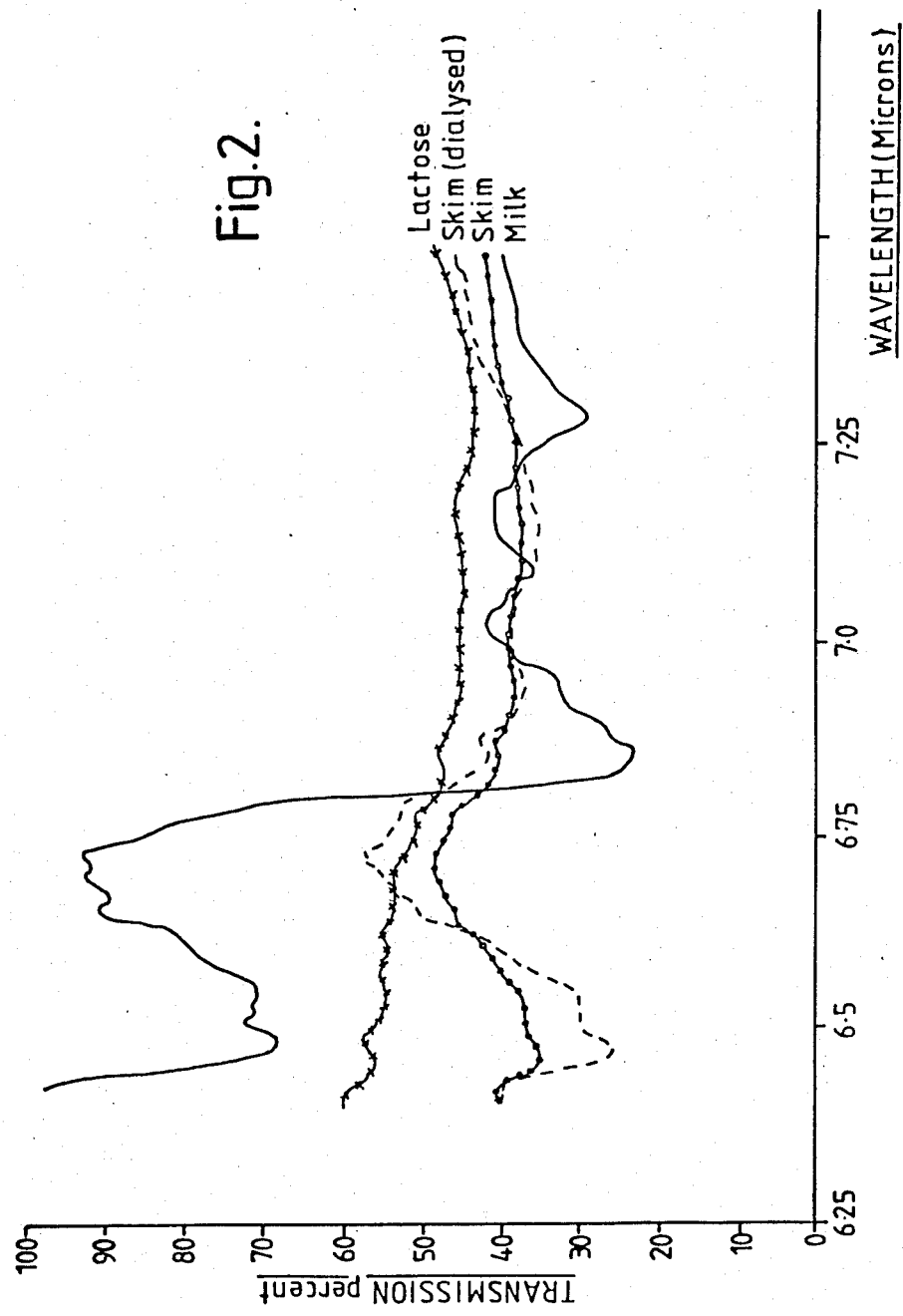
FIG. 2 shows spectra of a lactose solution against water and a protein solution/suspension against water.
Figure 3:
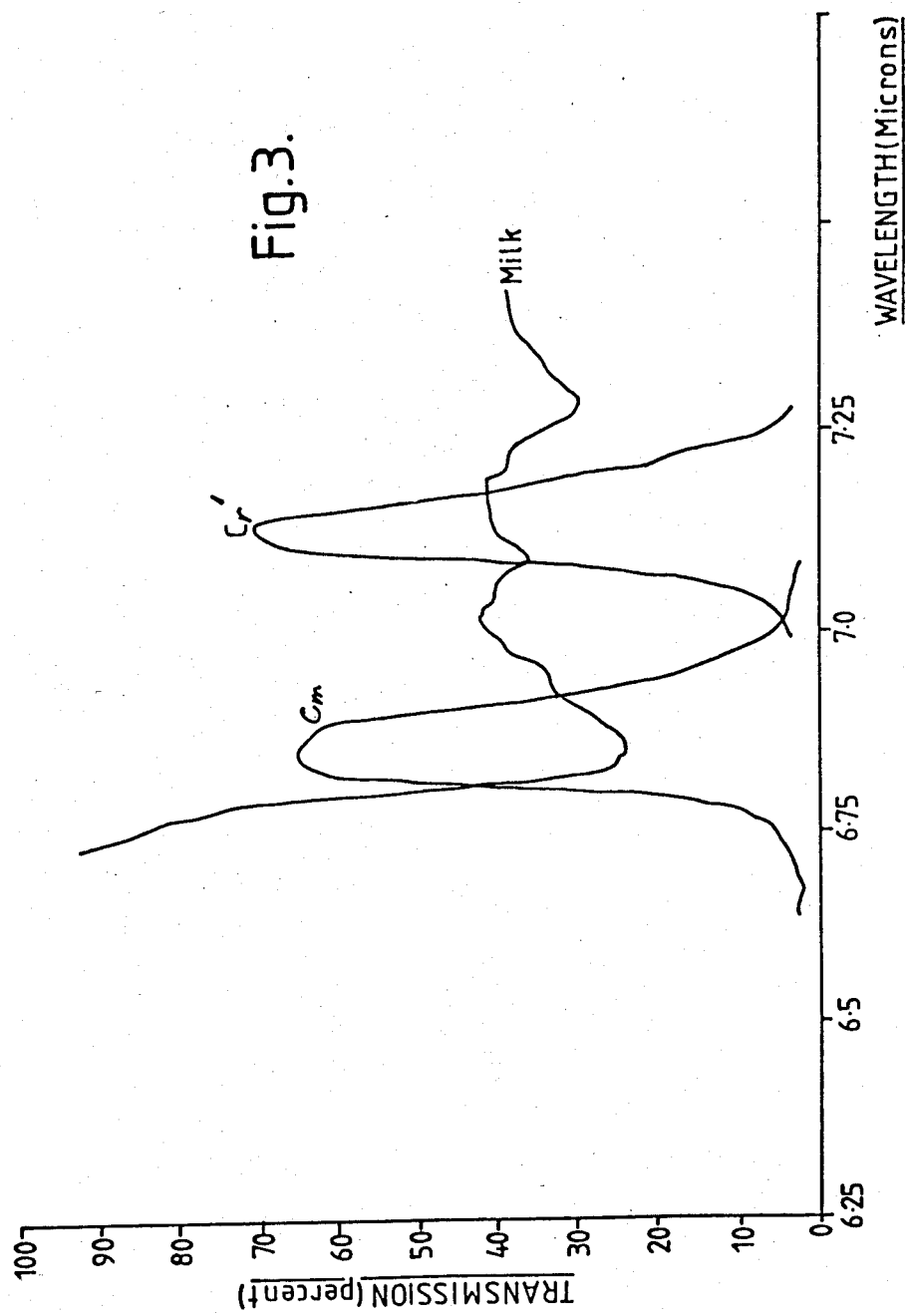
FIG. 3 shows a spectrum similar to that of FIG. 1 illustrating a different reference filter wavelength.

From the spectra illustrated in FIG. 2, it is apparent that good results should be obtained by selecting a reference filter Cr at about the 7.1 micron band. Accordingly, a MULTISPEC instrument was provided with a sample filter Cm as described in Example 1, and a reference filter Cr' (FIGS. 3 and 4) having a transmission characteristic at about 7.12 microns. As before the instrument was linearized and calibrated in the conventional manner. FIG. 3 illustrates the wavelengths of the sample and reference filters, and the good results were obtained with this reference wavelength also.

Figure 5:
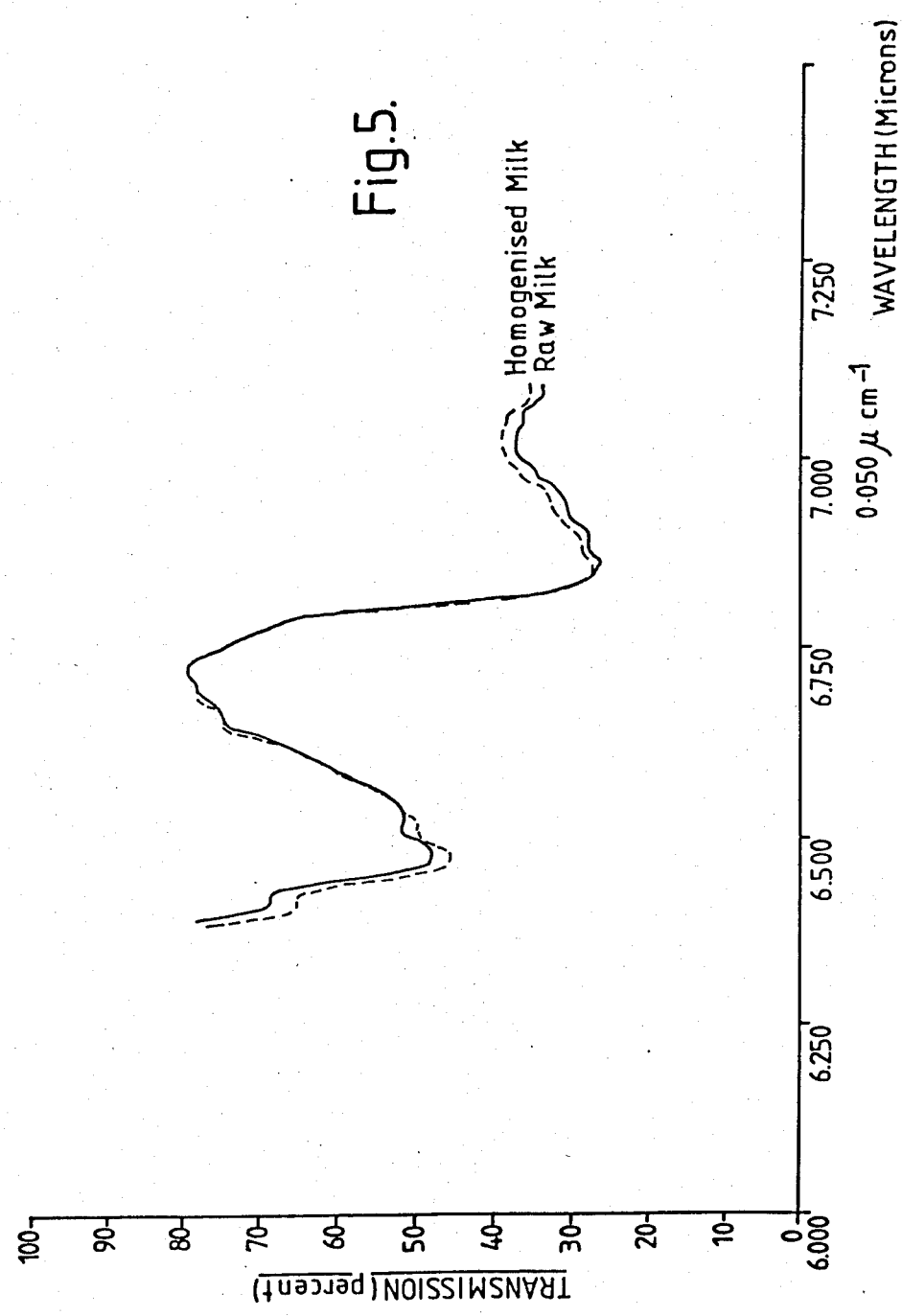
FIG. 5 illustrates spectra of homogenized and unhomogenized milk samples.

FIG. 5 illustrates different spectra for raw milk and homogenized milk against water in the 6.25 to 7.25 micron wavelength range, from which close correlation between the two can be observed. Table 3 shows the effect of degree of homogenization (as measured by homogenization pressure in the MULTISPEC instrument homogenizer) on raw fat readings $F_o$ for various measurement wavelengths. It can be seen from Table 3 that the accuracy of measurement at both of the 3.48 and 5.73 micron wavelengths declines radically at the lowest homogenization pressure, whereas at the preferred 6.84 micron wavelength of the present invention little error is introduced. Thus, measurement of milkfat concentration at the 6.84 micron wavelength in accordance with the invention significantly reduces dependence upon substantial and accurate homogenization, which can be a problem as an instrument wears.

Table 2 below illustrates the effect of lipolysis on raw fat readings $F_o$ for various measurement wavelengths. The degree of lipolysis is taken as a function of the age of the sample. It will be noted that, as the degree of lipolysis increases, errors are introduced at both of the 5.73 and 3.48 micron wavelengths, whereas at the preferred 6.84 micron wave band such errors are minimized. Thus, measurement of milkfat concentration at the 6.84 micron wavelength reduces the effect of lipolysis on measurement accuracy, and thus reduces criticality of measuring milkfat immediately after the sample is taken, which can be a problem in many cases.

Reference has been made in the specification to the "6.84 micron wave band". By this is meant generally the band from 6.75 to 7.10 microns, preferably with a center about 6.84 microns. As is known in the infrared spectrometry field, the bandwidth of the filter chosen can be varied. Filters having bandwidths of 110 nanometers or less have been found to be suitable. As for the reference wavelengths, a reference wavelength in the range of 6.46 to 6.75 microns has been found suitable, as has a reference wavelength in the range of 7.0 to 7.20 microns, particularly 7.11 to 7.15 microns.

As discussed above, homogenization is less critical at the preferred 6.84 micron wavelength of the present invention as the Christenson effect, which is a change in apparent refractive index for a given wavelength, is reduced relative to measurement at the 3.4 micron and 5.73 micron wave bands. However, it is preferred that the average fat globule diameter in the emulsion should be no greater than 3.5 microns, which is well within the capabilities of standard homogenizers even under adverse wear and maintenance conditions.

Figure 6:
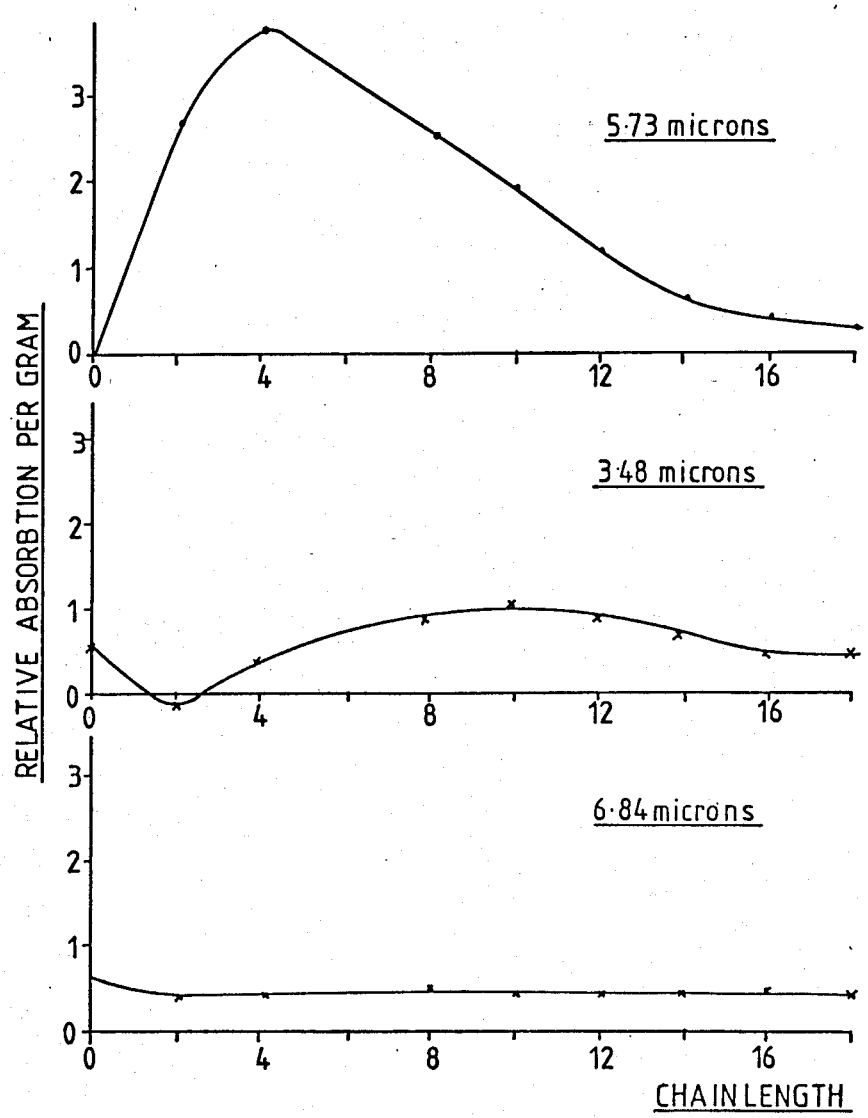
FIG. 6 shows three graphs illustrating the relative absorption of three wavelengths in comparison with fat chain length.

Referring to FIG. 6, measurements are made of triglycerides having varying chain lengths at each of the two previously-used wavelengths (3.48 and 5.73 microns) and the preferred 6.84 micron wavelength of the present invention. The relative absorption per gram at each wavelength was plotted against chain length of the triglyceride sample. It can be seen that the variation at the 5.73 micron sample wavelength is considerable, as is the variation at the 3.48 micron wave band. However, the relative absorption of the 6.84 micron wave band is virtually constant irrespective of chain length. Thus, it can be seen that errors arising through chain length variation in fat samples will be virtually eliminated using the preferred wavelength of the present invention.

A further advantage of the preferred wave band of the present invention is that an instrument measuring C-H can now employ a single blocking infrared filter over the infrared source, instead of each sample and/or reference filter having its own blocking element as is present practice. This enables the cost of the instrument to be reduced.

In further application of the principles of the present invention, a 6.68 micron reference wavelength was employed in combination with a 6.84 micron measurement wavelength. It was found, somewhat surprisingly, that a major portion of the fat reading was due to water displacement effects at the reference wavelength rather than simply absorption at the measurement wavelength. Applicant has obtained greatly improved sensitivity by measuring fat as a function of the ratio of the measurement reading to the reference reading.

TABLE 1

1. Equation Used:
$F_c = 1.355 F_o + 0.581 P_o - 0.871 L_o$
2. Estimated Values and Difference

| SAMPLE | SAMPLE | CHEMICAL | ESTIMATED | DIFFERENCE |

TABLE 1-continued

| NUMBER | TYPE | VALUE $F_m$(w/o) | VALUE $F_c$(w/o) | $(F_m - F_c)$ |
|---|---|---|---|---|
| 1 | MILK | 3.94 | 3.94 | .0026 |
| 2 | SKIMMED MILK | 0.11 | 0.12 | −.0094 |
| 3 | MILK | 4.03 | 4.00 | .0032 |
| 4 | MILK | 4.61 | 4.62 | −.0062 |
| 5 | HIGH FAT MILK | 5.50 | 5.52 | −.0205 |
| 6 | LACTOSE SOLN | 0.00 | 0.00 | −.0002 |

3. Standard Derivation of Difference (S D Accuracy) = 0.0182
4. Probable Precision = 0.0169

TABLE 2

| Sample Age (Mins) | Measurement Wavelength (Microns) | | |
|---|---|---|---|
| | 5.73 | 6.84 | 3.48 |
| 0 | 5.16 | 2.25 | 3.97 |
| 10 | 5.21 | 2.30 | 4.13 |
| 20 | 5.18 | 2.28 | 4.12 |
| 30 | 4.99 | 2.29 | 3.75 |
| 40 | 4.97 | 2.30 | 3.79 |
| 50 | 4.66 | 2.14 | 3.72 |
| 60 | 4.49 | 2.22 | 3.39 |

TABLE 3

| Homogenization (psi) | Measurement Wavelength (Microns) | | |
|---|---|---|---|
| | 5.73 | 6.84 | 3.48 |
| 2800 | 6.77 | 6.08 | 6.57 |
| 2700 | 6.78 | 6.06 | 6.59 |
| 2600 | 6.76 | 6.10 | 6.56 |
| 2400 | 6.71 | 6.06 | 6.53 |
| 2300 | 6.70 | 6.04 | 6.54 |
| 2100 | 6.31 | 6.04 | 5.88 |

The invention claimed is:

1. A method for direct infrared measurement of milkfat concentration in the range of 15 to 60 w/o in dairy products such as cream and ice cream, said method comprising the steps of:
 (a) transmitting infrared energy through a test sample of the dairy product,
 (b) determining infrared absorption of the sample at a first wave band characteristic of bending and scissoring of saturated carbon-hydrogen bonds in milkfat fatty acid chains, and
 (c) quantitatively determining fat concentration in the sample as a function of absorption at said first wave band.

2. The method set forth in claim 1 wherein said first wave band is in the range of about 6.75 to 7.1 microns.

3. The method set forth in claim 1 comprising the additional steps:
 (d) determining infrared absorption of the sample at a second wave band adjacent to said first wave band but not characteristic of saturated carbon-hydrogen bonds, and wherein said step (c) comprises the step comparing absorption at said first wave band to absorption at said second wave band.

4. The method set forth in claim 3 wherein said first wave band is centered at about 6.84 microns.

5. The method set forth in claim 4 wherein said second wave band is in the range of about 6.46 to 6.75 microns.

6. The method set forth in claim 4 wherein said second wave band is in the range of about 7.0 to 7.20 microns.

7. The method set forth in claim 6 wherein said second wave band is in the range of about 7.11 to 7.15 microns.

8. A method of measuring fat concentration in dairy products comprising the steps of: irradiating a test sample with infrared energy, determining infrared absorption of said sample at a first wave band of said infrared energy characteristic of bending and scissoring of saturated carbon-hydrogen bonds, and quantitatively determining the fat concentration in said sample as a function of absorption at said first wave band.

9. The method set forth in claim 8 wherein said first wave band is from 6.75 to 7.1 microns.

10. The method set forth in claim 9 wherein said first wave band is at about 6.84 microns.

11. The method set forth in claim 10 wherein said method comprises the additional step of determining infrared absorption of said sample at a second wave band in the range of about 6.46 to 6.75 and 7.0 to 7.20 microns, and wherein said step of quantitatively determining fat concentration comprises the step of comparing absorption at said first wave band to absorption at said second wave band.

12. The method set forth in claim 11 wherein said second wave band is in the range of about 7.11 to 7.15 microns.

13. The method set forth in claim 11 comprising the additional step, prior to irradiating said sample, of reducing diameter of fat globules in said sample to not greater than 3.5 microns.

14. The method set forth in claim 10 wherein said first wave band has a band width of not greater than 110 mm.

* * * * *